(12) United States Patent
Ono et al.

(10) Patent No.: US 7,863,024 B2
(45) Date of Patent: Jan. 4, 2011

(54) PROCESS FOR PRODUCING HIGHLY UNSATURATED FATTY ACID-CONTAINING LIPID

(75) Inventors: Kazuhisa Ono, Higashihiroshima (JP); Tsunehiro Aki, Higashihiroshima (JP); Kenichi Higashiyama, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 612 days.

(21) Appl. No.: 10/512,557

(22) PCT Filed: Apr. 25, 2003

(86) PCT No.: PCT/JP03/05408

§ 371 (c)(1), (2), (4) Date: Feb. 15, 2005

(87) PCT Pub. No.: WO03/091445

PCT Pub. Date: Nov. 6, 2003

(65) Prior Publication Data

US 2005/0191734 A1 Sep. 1, 2005

(30) Foreign Application Priority Data

Apr. 26, 2002 (JP) ............................ 2002-126757

(51) Int. Cl.
*C12P 1/00* (2006.01)
*C12P 7/64* (2006.01)

(52) U.S. Cl. ........................................ 435/134; 435/41

(58) Field of Classification Search ....................... None
See application file for complete search history.

(56) References Cited

U.S. PATENT DOCUMENTS

| | | | |
|---|---|---|---|
| 2,346,011 A | 4/1944 | Damm | |
| 4,783,408 A | 11/1988 | Suzuki et al. | |
| 4,857,329 A | 8/1989 | Sako et al. | |
| 4,870,011 A | 9/1989 | Suzuki et al. | |
| 4,885,249 A | 12/1989 | Buxton et al. | |
| 4,916,066 A | 4/1990 | Akimoto et al. | |
| 5,015,579 A | 5/1991 | Yamaguchi et al. | |
| 5,026,644 A | 6/1991 | Manoh et al. | |
| 5,034,321 A | 7/1991 | Nakajima et al. | |
| 5,053,222 A | 10/1991 | Takasu et al. | |
| 5,093,249 A | 3/1992 | Nakajima et al. | |
| 5,128,250 A | 7/1992 | Akimoto et al. | |
| 5,164,308 A | 11/1992 | Kyle | |
| 5,260,213 A | 11/1993 | Harman et al. | |
| 5,322,780 A * | 6/1994 | Kawashima et al. | 435/134 |
| 5,376,541 A | 12/1994 | Kawashima et al. | |
| 5,401,646 A | 3/1995 | Shinmen et al. | |
| 5,583,019 A | 12/1996 | Barclay | |
| 5,658,767 A | 8/1997 | Kyle | |
| 6,150,144 A * | 11/2000 | Akimoto et al. | 435/134 |
| 6,746,857 B2 * | 6/2004 | Higashiyama et al. | 435/134 |
| 6,958,229 B2 * | 10/2005 | Suzuki et al. | 435/134 |
| 7,157,254 B1 * | 1/2007 | Akimoto et al. | 435/134 |

FOREIGN PATENT DOCUMENTS

| | | |
|---|---|---|
| CH | CN 1323904 A | 11/2001 |
| CN | 1323904 A | 5/2000 |
| CN | 1323904 A | 11/2001 |
| CN | 1323904 A * | 11/2001 |
| EP | 0 252 716 | 1/1988 |
| EP | 0 269 351 A2 | 6/1988 |
| EP | 0 276 982 A2 | 8/1988 |
| EP | 0 223 960 B1 | 7/1992 |
| EP | 0 252 716 B1 | 1/1993 |
| EP | 0 276 541 B1 | 3/1993 |
| EP | 0 332 423 B1 | 10/1995 |
| EP | 0 726 321 A2 | 8/1996 |
| EP | 0 535 939 B1 | 7/1997 |
| EP | 0 790 056 B1 | 11/2004 |
| GB | 2 013 087 A | 8/1979 |
| JP | 52-64484 | 5/1977 |
| JP | 57-144986 | 9/1982 |
| JP | 59-130191 | 7/1984 |
| JP | 60-126091 | 7/1985 |
| JP | 63-012290 | 1/1988 |
| JP | 63-12290 | 1/1988 |
| JP | 63-14696 | 1/1988 |

(Continued)

OTHER PUBLICATIONS

Abouzed et al. Applied and Environmental Microbiology, Nov. 1986, p. 1055-1059.*

(Continued)

*Primary Examiner*—N. M. Minnifield
*Assistant Examiner*—Oluwatosin Ogunbiyi
(74) *Attorney, Agent, or Firm*—Drinker Biddle & Reath, LLP

(57) ABSTRACT

The present invention provides a process for producing a highly unsaturated fatty acid-containing lipid which is less expensive than existing ones, which comprises culturing a microorganism belonging to the genus *Mortierella* with the use of, as a medium carbon source, a saccharified starch, which is less expensive than glucose, does not contribute to an increase in osmotic pressure of the culture medium, and can be utilized by the *Mortierella* microorganism, and collecting a highly unsaturated fatty acid-containing lipid from the culture.

8 Claims, No Drawings

FOREIGN PATENT DOCUMENTS

| | | |
|---|---|---|
| JP | 63-014696 | 1/1988 |
| JP | 63-014697 | 1/1988 |
| JP | 63-14697 | 1/1988 |
| JP | 63-044891 | 2/1988 |
| JP | 63-133994 | 6/1988 |
| JP | 63-240791 | 10/1988 |
| JP | 1-199588 | 8/1989 |
| JP | 2-86789 | 3/1990 |
| JP | 3-49688 | 3/1991 |
| JP | 05-091887 | 4/1993 |
| JP | 5-91887 | 4/1993 |
| JP | 05-091888 | 4/1993 |
| JP | 5-91888 | 4/1993 |
| JP | 5-91889 A | 4/1993 |
| JP | 6-153970 | 6/1994 |
| JP | 06153970 A | 6/1994 |
| JP | 06-339368 | 12/1994 |
| JP | 7-289143 | 7/1995 |
| JP | 8-214893 | 8/1996 |
| JP | 2001-61490 | 3/2001 |
| JP | 8-214893 | 10/2005 |
| WO | WO 91/07498 | 5/1991 |
| WO | WO 92/13086 | 8/1992 |
| WO | WO 94/01001 | 1/1994 |
| WO | WO 98/39468 | 9/1998 |

OTHER PUBLICATIONS

Farid et al. J .Basic Microbiol. 42 (2002) 3, 162-171.*
Ohdan et al Applied and Environmental Microbiology, Oct. 1999, p. 4652-4658.*
Definition of auxiliary -meriam-websters online dictionary: http: www.merriam-webster.com/cgi-bin/dictionary?book=dictionary$va=auxiliary. Retrieved Feb. 10, 2008.*
Shinmen et al Appl Microbiol Biotechnol 1989 31:11-16.*
Arasaratnam et al. Starch/Starke 50 1998 Nr. 2-3, S. 95-98.*
Eroshin et al World Journal of Microbiology and Biotechnology 12, 91-96.*
(Comparable. (2009). In Merriam-Webster Online Dictionary. Retrieved Dec. 2, 2009, from http://www.merriamwebster.com/dictionary/comparable).*
Shinmen et al., "Production of Arachidonic acid by *Mortierella* fungi" Applied Microbiology and Biotechnology, (1989) 31:11-16.
Aki et al., "Production of Arachidonic Acid by Filamentous Fungus, *Mortierella alliacae* Strain YN-15," JOACS, vol. 78, No. 6, (2001), pp. 599-604.
Lindberg et al., "Production of γ-linolenic acid by fungus *Mucor rouxii* on cheap nitrogen and carbon sources," Appl. Microbiol. Biotechnol. (1991), 36:26-28, Springer Verlag, Berlin, Germany.
Shah et al., "Starch Hydrolysate, an Optimal and Economical Source of Carbon for the Secretion of Citric Acid by *Yarrowia lipolytica* (DS-1)," Starch, 45 (1993). No. 3, S. pp. 104-109.
Kurosawa et al., "Ethanol Production from Starch by a Coimmobilized Mixed Culture System of *Aspergillus awamori* and *Saccharomyces cerevisiae*," Biotechnology and Bioengineering, vol. 33, (1989) pp. 716-723, Wiley, New York.
Lindberg et al., "Effect of temperature and glucose supply on the production of polyunsaturated fatty acids by the fungus *Mortierella alpina* CBS 343.66 in fermentor cultures," Appl. Microbiol. Biotechnol. (1993) 39, pp. 450-455, Springer Verlag, Berlin, Germany.
Zhu et al., "An inexpensive medium for production of arachidonic acid by *Mortierella alpina*," J. Ind. Microbiol. Biotechnol. (2003), 30, pp. 75-79.
International Search Report issued Jul. 15, 2003, in PCT/JP03/05403.
Carlson et al., "Arachidonic acid status correlates with first year growth in preterm infants," Proc. Natl. Acad. Sci. USA, Feb. 1, 1993, vol. 90, No. 3, pp. 1074-1077 (Abstract).

Sakuradani et al., "Improvement of arachidonic acid production by mutants with lower n3 desaturation activity derived from *Mortierella alphina* 1S-4," Appl. Microbiol. Biotechnol. 2004, vol. 66, pp. 243-248.
Jang et al., "Polyunsaturated fatty acid production with *Mortierella alpina* by solid substrate fermentation," Botanical Bull. Acad. Sin. (2000) vol. 41, pp. 41-48.
Stred'anská et al., "Arachidonic acid production by *Mortierella alpina* grown on solid substrates," World Journal of Microbiology and Biotechnology, (1993) vol. 9, pp. 511-513.
Hansson et al., "Effect of culture conditions on mycelial growth and production of γ-linolenic acid by the fungus *Mortierella ramanniana*," Appl. Microbiol Biotechnol (1988) vol. 28, pp. 240-246.
Thurmond et al., "Polyunsaturated fatty acid-specific elongation enzymes," Biochemical Society, (2000), vol. 28, part 6, pp. 658-660.
Tanaka et al., "Purification and Characterization of a Novel Fungal α-Glucosidase from *Mortierella alliacea* with High Starch-hydrolytic Activity," Biosci. Biotechnol. Biochem., (2002) vol. 66, No. 11, pp. 2415-2423.
Supplemental European Search Report mailed Feb. 15, 2010 EP Application No. 03723218.8.
Ratledge, Microbial routes to lipids, Biotechnology Aspects of Lipids, vol. 17(6), Dec. 1989, pp. 1139-1141.
Kendrick et al., "Lipids of Selected Molds Grown for Production of n-3 and n-6 Polyunsaturated Fatty Acids," Lipids, vol. 27(1), 1992, pp. 15-20.
Jareonkitmongkol et al., "Production of Dihomo-Δ-Linolenic Acid by a Δ5-Desaturase-Defective Mutant of *Mortierella alpina* 1S-4," Applied and Environmental Microbiology, Jul. 1992, pp. 2196-2200.
Jareonkitmongkol et al., "Fatty acid desaturation-defective mutants of an arachidonic-acid-producing fungus, *Mortierella alpina* 1S-4," Journal of General Microbiology, 1992, vol. 138, pp. 997-1002.
Shimizu et al., "Biosynthesis of C-20 Polyunsaturated Fatty Acids by *Mortierella* Fungi," pp. 158-165, 1991.
Shimizu et al., "Sesamin Is a Potent and Specific Inhibitor of Δ5 Desaturase in Polyunsaturated Fatty Acid Biosynthesis," Lipids, vol. 26(7), 1991, pp. 512-516.
Shimizu et al., "Production of a novel ωl-eicosapentaenoic acid by *Mortierella alpina* 1S-4 grown on 1-hexadecene," Arch. Microbiol. vol. 156, 1991, pp. 163-166.
Ratledge, "The Potential of Microorganisms for Oil Production—A Review of Recent Publications," World Conference on Emerging Technologies in the Fats and Oils Industry, ed. by Baldwin, 1986, American Oil Chemists' Society, pp. 325-330.
Totani et al., "An Improved Method of Arachdonic Acid Production by *Mortierella alpina*," J. Jpn. Oil Chem. Soc., pp. 328-331.
Yamada et al., "Production of Arachdonic Acid and Eicosapentaenoic Acid by Microorganisms," American Oil Chemists Society, 1988, pp. 172-177.
Fragrance Journal, 1996-6, pp. 67-75 (partial translation).
Fukui, "Selection and Breeding of Microorganisms Secreting and Producing Fuel Lipids," Bio-Industry, vol. 12, No. 3, 1995, pp. 36-46 (partial translation).
Demain et al., "Manual of Industrial Microbiology and Biotechnology," 1986, American Society for Microbiology, p. 188.
Stedman's Medical Dictionary, 1995, (Williams and Wilkins Baltimore, MD), pp. 121 and 1851.
Certik et al., "Desaturase-defective fungal mutants: useful tools for the regulation and overproduction of polyunsaturated fatty acids," Tibtech, Dec. 1998, vol. 16, pp. 500-505.
Sigma Cell Culture Reagents Catalogue, 1992, pp. 282 and 286.
Li et al., "Process for Production of Arachidonic Acid Concentrate by a Strain of *Mortierella alphina*," The Canadian Journal of Chemical Engineering, vol. 73, Feb. 1995, pp. 135-139.
Totani et al., "Industrial Production of Arachidonic Acid by *Mortierella*," Chapter 4, pp. 52-60, 1992, in Industrial Application of Single Cell Oils. David J. Kyle and Collin Ratledge, AOCS Publishing.

* cited by examiner

US 7,863,024 B2

PROCESS FOR PRODUCING HIGHLY UNSATURATED FATTY ACID-CONTAINING LIPID

TECHNICAL FIELD

The present invention relates to a process for producing a highly unsaturated fatty acid-containing lipid, comprising culturing a microorganism belonging to the genus *Mortierella* producing a highly unsaturated fatty acid (hereinafter, referred to as a *Mortierella* microorganism) with the use of a saccharified starch as a carbon source of the culture medium, and collecting a highly unsaturated fatty acid-containing lipid from the culture.

BACKGROUND TECHNIQUE

In the present specification, an unsaturated fatty acid refers to a fatty acid having one or more double bond(s) in a carbon chain and, among this, the fatty acid having a carbon number of 18 or more and two or more double bonds is generally referred to as "highly unsaturated fatty acid". Examples of the highly unsaturated fatty acid include γ-linolenic acid, dihomo-γ-linolenic acid, arachidonic acid, eicosapentaenoic acid, mead acid, 6,9-octadecadienoic acid, 8,11-eicosadienoic acid, etc. Most of the highly unsaturated fatty acids generated by a *Mortierella* microorganism are produced as fatty acids constituting triglyceride and, besides this, also as fatty acids constituting various lipids such as diglyceride, monoglyceride, free fatty acid, phospholipid, etc. As used herein, the highly unsaturated acid-containing lipid is a mixture of lipids containing these various highly unsaturated fatty acids, and an amount of arachidonic acid production is a value obtained by converting the amount of arachidonic acid existing as fatty acids constituting those various lipids into the amount of free fatty acids. In addition, a mixture of oligoglucose and glucose, which is obtained by treating a starch with a saccharifying enzyme such as amylase, is referred to as "saccharified starch", a sugar degrading enzyme such as amylase which is used for producing a saccharified starch is referred to as "saccharifying enzyme", and treatment of a starch with the enzyme is referred to as "saccharification". A degradation degree of starch by saccharification is referred to as "saccharification degree", and the saccharification degree is expressed by the ratio of reducing sugar/total sugar (%) of the saccharified starch. For example, a ratio of reducing sugar/total sugar of 50% indicates that the average chain length of α-glucan in the saccharified starch is 2.

Highly unsaturated fatty acids such as arachidonic acid, along with DHA (docosahexaenoic acid), have drawn attention from a nutritional point of view, especially as a component necessary for the growth of a baby. Lanting et al. conducted a 9-year follow-up study of babies who had been breastfed and babies who had been powdered formula-fed for three weeks or longer after birth. They examined the incidence of a minor neurological dysfunction from behavioral aspects and, as a result, reported that the incidence of neurological dysfunction in children who were powdered formula-fed was 2-fold that of children who were breastfed (LANCET, vol.344, 1319-1322 (1994)). According to the report, the result is due to the fact that highly unsaturated fatty acids such as DHA, arachidonic acid, etc., which are present in breast milk but are hardly present in powdered formula, are involved in the development of a baby's brain. Besides, results that highly unsaturated fatty acids are involved in the development of brain and retina of a neonate, have been frequently reported (Carlson et al., Broc. Natl. Acad. Sci. 90:1073-1077(1993)), and the importance of those highly unsaturated fatty acids is drawing attention from a nutritional viewpoint for a premature baby and a neonate.

Highly unsaturated fatty acids are widely distributed in the living world and, for example, arachidonic acid has been separated from a lipid extracted from animal adrenal gland or liver. However, since a content of the highly unsaturated fatty acid in animal organs is small, the extraction and separation of highly unsaturated fatty acids from an animal organ is not a sufficient method for supplying a large amount of highly unsaturated fatty acids. For this reason, methods of obtaining highly unsaturated fatty acids by culturing various microorganisms have been developed. Among the microorganisms, a *Mortierella* microorganism is known as a microorganism producing a highly unsaturated fatty acid-containing lipid such as arachidonic acid, dihomo-γ-linolenic acid, eicosapentaenoic acid, etc., and a process for producing a highly unsaturated fatty acid-containing lipid by fermentation using this microorganism has been developed (JP-A No. 63-44891, JP-A No. 63-12290, JP-A No. 63-14696, JP-A No. 63-14697). Further, a process for producing a mead acid using a mutant in which Δ12 desaturation enzyme activities of a *Mortierella* microorganism are reduced or lost has also been known (JP-A No. 5-91888). In addition, a process for producing dihomo-γ-linolenic acid using a mutant in which Δ5 desaturation enzyme activities are reduced or lost, which is obtained by subjecting a *Mortierella* microorganism to mutation induction, has also been known (JP-A No. 5-91887).

Although it has already been known that a *Mortierella* microorganism has the ability to assimilate a starch, since its starch-assimilating ability is inferior as compared to the glucose-utilizing ability, glucose has been widely used as a medium carbon source for such microorganism( Shinmen et al., Appl. Microbiol. Biotechnol. 31:11-16 (1989), Aki et al., JAOCS 78:599-604 (2001)). As a result of paying attention to the starch-utilizing ability of a *Mortierella* microorganism, it has been reported that a secreted starch-degrading enzyme is isolated and purified, and the starch-degrading enzyme is identified to be α-glucosidase (Tanaka et al., Bulletin of Japan Society of Bioscience, Biotechnology, and Agrochemistry, March 1999). However, α-glucosidase, which is an exo-type amylase having a degradation pattern of cleavage of glucose units from a non-reducing end of α-glucan, has a low activity to degrade high-molecular α-glucan, a representative of which is a starch, and has a high activity of degrading an oligoglucose composed of several glucoses. This is thought to be one of the reasons why the starch-utilizing ability of a *Mortierella* microorganism is lower than the glucose-utilizing ability. On the other hand, when glucose is used as a carbon source, since an increase in osmotic pressure due to high concentration of glucose in the culture medium has adverse influence on the growth of cells of, and the productivity of a highly unsaturated fatty acid-containing lipid of a *Mortierella* microorganism, there has been widely used a method comprising culturing the microorganism with low concentration glucose and sequentially adding glucose during culture to compensate the utilized glucose (Shinmen et al., Appl. Microbiol. Biotechnol. 31:11-16(1989)). In addition, an attempt to produce a highly unsaturated fatty acid-containing lipid using a *Mortierella* microorganism having resistance to high concentration glucose (International Publication No. WO98/39468) has also been tried. A carbon source of the culture medium accounts for the majority of raw material costs and, if this can be changed to a raw material which is less expensive than glucose, the cost for producing a highly unsaturated fatty acid-containing lipid can be reduced. When a starch which is a raw material for glucose is used as a medium carbon source, the raw material cost can be reduced, however, α-glucosidase produced by a *Mortierella* microorganism has the low activity of degrading a starch as described above and, therefore, the starch can not be sufficiently assimilated by said microorganism. In addition, a culture medium containing glucose at a high concentration has a high osmotic pressure, and this becomes a cause for delay of the growth of a *Mortierella* microorganism, reduction in its productivity of a highly unsaturated fatty acid-containing lipid and change in the morphological form. Therefore, it is difficult to produce a highly unsaturated fatty acid-containing lipid at a low cost by a batch culture method in which glucose is not sequentially added during culturing and glucose is contained at a high concentration at the time of the initiation of culturing. As a means to solve this problem, a feeding culture method in which glucose is sequentially added to the culture medium is used. However, since the feeding culture not only requires an additional apparatus for sequentially adding glucose but also increases the number of works and working time in the culturing step, this method increases the cost for producing a highly unsaturated fatty acid-containing lipid. In addition, although glucose is produced by enzymatic degradation of starch with various amylases, it is necessary to isolate and purify glucose after the enzymatic treatment. Thus, the cost for enzymatic treatment and isolation and purification makes glucose more expensive than starch.

Production of a highly unsaturated fatty acid-containing lipid utilizing a starch or a soluble starch as a medium carbon source has been reported (Shinmen et al., Appl. Microbiol. Biotechnol. 31:11-16(1989), Aki et al., JAOCS 78:599-604 (2001)). However, the yield of a highly unsaturated fatty acid-containing lipid per sugar in said culture medium is lower than that of the case where the same amount of glucose is used as a carbon source due to the incomplete assimilation of a starch or a soluble starch.

DISCLOSURE OF THE INVENTION

The present invention provides a process for producing a highly unsaturated fatty acid-containing lipid at a lower cost than existing ones, comprising the use of a medium carbon source, which is less expensive than glucose, does not participate in increasing osmotic pressure of the culture medium and can be assimilated by a *Mortierella* microorganism.

The α-glucosidase produced by a *Mortierella* microorganism has a low activity of degrading a starch as described above. In order to use a starch as a medium carbon source, it is necessary to degrade the starch to a saccharified starch which can be easily degraded by α-glucosidase produced by a *Mortierella* microorganism. However, when a starch is completely degraded to glucose, an increase in osmotic pressure due to an increase of monosaccharide is caused, having various negative influences on the production of a highly unsaturated fatty acid-containing lipid as described above. Then, the present inventors came up with an idea of controlling the average chain length of an oligoglucose in a saccharified starch at a proper length which can be easily degraded by α-glucosidase produced by a *Mortierella* microorganism, by selecting a sugar degrading enzyme for saccharification of starch and conditions of saccharification with the enzyme. The present inventors compared the productivity of a highly unsaturated fatty acid-containing lipid, which was extracted from the cells obtained by culturing a *Mortierella* microorganism using, as a medium carbon source, a saccharified starch prepared by saccharification of a starch using various sugar degrading enzymes under a variety of conditions, with the productivity of the case where culturing is performed by a batch culture using the same amount of starch or glucose as a medium carbon source and with the productivity of the case where culturing is performed by a feeding culture by adding the same amount of glucose as a medium carbon source. As a result, the present inventors found that, when a saccharified starch is used as a carbon source, a higher productivity is exhibited as compared to the case of the batch culture using a starch or glucose as a medium carbon source, and that the productivity was equivalent to that of the feeding culture using glucose as a medium carbon source. The present inventors conducted further studies and finally completed the present invention.

That is, the present invention relates to:

(1) a process for producing a highly unsaturated fatty acid-containing lipid, which comprises culturing a microorganism belonging to the genus Mortierella with the use of a culture medium containing a saccharified starch, and collecting a highly unsaturated fatty acid-containing lipid from the culture, (2) the process according to the above (1), wherein the saccharified starch is obtained by treating a starch or a soluble starch with a saccharifying enzyme;

(3) a process for producing a highly unsaturated fatty acid-containing lipid, which comprises culturing a microorganism belonging to the genus *Mortierella* with the use of a culture medium containing (a) a starch or a soluble starch and (b) a saccharifying enzyme, and collecting a highly unsaturated fatty acid-containing lipid from the culture;

(4) a process for producing a highly unsaturated fatty acid-containing lipid, which comprises mixed-culturing a *Mortierella* microorganism and a microorganism producing a saccharifying enzyme with the use of a culture medium containing a starch or a soluble starch, and collecting a highly unsaturated fatty acid-containing lipid from the culture;

(5) the process according to the above (4), wherein the microorganism producing a saccharifying enzyme is a microorganism belonging to the genus *Aspergillus*;

(6) the process according to the above (5), wherein the microorganism belonging to the genus *Aspergillus* is *Aspergillus oryzae* or *Aspergillus kawachii*;

(7) the process according to any one of the above (1) to (6), wherein the microorganism belonging to the genus *Mortierella* is a microorganism belonging to the subgenus *Mortierella*;

(8) the process according to the above (7), wherein the microorganism belonging to the subgenus *Mortierella* is *Mortierella alpina* or *Mortierella alliacea*; and (9) the process according to any one of the above (1) to (8), wherein the highly unsaturated fatty acid is one or more fatty acid(s) selected from the group consisting of γ-linolenic acid, dihomo-γ-linolenic acid, arachidonic acid, eicosapentaenoic acid, mead acid, 6,9-octadecadienoic acid and 8,11-eicosadienoic acid.

BEST MODE FOR CARRYING OUT THE INVENTION

A microorganism used in the present invention may be any microorganism belonging to the genus *Mortierella* which can produce a lipid containing highly unsaturated fatty acids. As such a microorganism, bacterium strains described, for example, in MYCOTAXON, Vol.XLIV, No. 2, pp.257-265 (1992) can be used, and specific examples thereof include microorganisms belonging to the subgenus *Mortierella* such as *Mortierella elongata* IF08570, *Mortierella exigua* IF08571, *Mortierella hygrophila* IF05941, *Mortierella*

*alpina* IF08568, ATCC16266, ATCC32221, ATCC42430, CBS 219.35, CBS224.37, CBS250.53, CBS343.66, CBS527.72, CBS528.72, CBS529.72, CBS608.70, CBS754.68, etc. and microorganisms belonging to the subgenus Micromucor such as *Mortierella isabellina* CBS194.28, IF06336, IF07824, IF07873, IF07874, IF08286, IF08308, IF07884, *Mortierella nana* IF08190, *Mortierella ramanniana* IF05426, IF08186, CBS112.08, CBS212.72, IF07825, IF08184, IF08185, IF08287, *Mortierella vinacea* CBS236.82, etc.

Any of those strains can be obtained from Institute for Fermentation, Osaka City, and American Type Culture Collection (ATCC) in USA, and Centraalbureau voor Schimmelcultures (CBS) in Netherlands without any restriction. Alternatively, a strain *Mortierella elongata* SAM0219 (National Institute of Bioscience and Human-Technology, deposition No.8703) (National Institute of Bioscience and Human-Technology, conditional deposition No.1289) which was isolated from a soil by the present inventors may be used. Any strain belonging to those type cultures or strains isolated from the natural world can be used as they are. Also, as the microorganism used in the present invention, a mutant or a genetically recombinant strain of a *Mortierella* microorganism (wild strain) may be used. Among them, preferable examples include a mutant and a genetically modified strain in which, when cultured under the same culturing conditions as those of a wild strain, the amount of particular or all highly unsaturated fatty acid(s) in a lipid is larger, or a total lipid amount is larger, as compared to that of a highly unsaturated fatty acid lipid produced by the original wild strain, or those which can attain both of them. Examples of a mutant which contains larger amount of a particular highly unsaturated fatty acid in a lipid include *Mortierella alpina* SAM1861 which lacks the Δ12 desaturation enzyme activity (National Institute of Bioscience and Human-Technology, conditional deposition No. 3590, FERM BP-3590), and *Mortierella alpine* SAM1860 which lacks the Δ5 desaturation enzyme activity (National Institute of Bioscience and Human-Technology, conditional deposition No. 3589, FERMBP-3589). Alternatively, *Mortierella* SAM2197having resistance to high concentration of glucose (FERM BP-6261) may be used.

Examples of a process for producing a highly unsaturated fatty acid-containing lipid of the present invention include the three embodiments of (i) culturing the aforementioned *Mortierella* microorganism with the use of a culture medium containing a saccharified starch, and collecting a highly unsaturated fatty acid-containing lipid from the culture, (ii) culturing the aforementioned *Mortierella* microorganism with the use of a culture medium containing (a) a starch or a soluble starch and (b) a saccharifying enzyme, and collecting a highly unsaturated fatty acid-containing lipid from the culture, or (iii) mixed-culturing the aforementioned *Mortierella* microorganism and a microorganism producing a saccharifying enzyme (hereinafter, referred to as saccharifying enzyme-producing microorganism) with the use of a culture medium containing a starch or a soluble starch, and collecting a highly unsaturated fatty acid-containing lipid from the culture. Each embodiment will be separately explained below.

As a first embodiment of the present invention, a process for producing a highly unsaturated fatty acid-containing lipid, which comprises culturing the aforementioned *Mortierella* microorganism with the use of a culture medium containing a saccharified starch, and collecting a highly unsaturated fatty acid-containing lipid from the culture will be described. As mentioned above, the use of a saccharified starch which is obtained by saccharification of a starch in advance as a carbon source of the culture medium, has advantages that said saccharified starch is easily assimilated by a *Mortierella* microorganism and an increase of osmotic pressure in the culture medium is suppressed, whereby the yield of a highly unsaturated fatty acid-containing lipid per carbon source can be increased.

Culturing of a single *Mortierella* microorganism in the present embodiment may be performed according to the conventional method, except that a saccharified starch is used as a carbon source of the culture medium. For example, there can be exemplified a method in which a liquid culture medium or a solid culture medium is inoculated with a spore or a hypha of the *Mortierella* microorganism or a culture solution obtained by pre-culture, followed by culturing.

A culture medium for culturing a microorganism in the said embodiment is not particularly limited as far as the culture medium contains a saccharified starch as a medium carbon source. Inter alia, it is desirable that the saccharified starch used as a medium carbon source has the saccharification degree at which it can be most easily degraded by α-glucosidase produced by the Mortierella microorganism which is to be cultured, that is, an average chain length of oligoglucose in a saccharified starch. Specifically, in view of an increase in osmotic pressure and a chain length of oligoglucose in the saccharified starch which can be assimilated by a *Mortierella* microorganism, it is preferable to use the saccharified starch of which reducing sugar/total sugar ratio, i.e., a saccharification degree, is about 2 to 90%, preferably about 30 to 90%.

A saccharified starch can be obtained by treating a starch or a soluble starch with a saccharifying enzyme and, by further selecting the saccharifying enzyme and setting the conditions of saccharification with the enzyme, the saccharified starch having the above desired saccharification degree can be obtained. A saccharifying enzyme is not particularly limited as far as it is a sugar degrading enzyme which can degrade starch, etc., but an endo-type amylase such as α-amylase having random degradation patterns, or an exo-type amylase such as β-amylase which cleaves maltose units from an end of a starch molecule is preferable. Alternatively, saccharifying enzymes having different actions of mechanism may be used by combining thereof. A saccharifying enzyme used in saccharification can be obtained by culturing a microorganism producing the saccharifying enzyme, and obtaining the enzyme from the culture by the known method. Alternatively, a commercially available saccharifying enzyme may be used. Examples of commercially available saccharifying enzymes include an α-amylase such as amylase AD "Amano"1 (manufactured by Amano Enzyme Inc.) and a pullulanase such as Pullulanase "Amano"3 (manufactured by Amano Enzyme Inc.). Also, the saccharified starch can be obtained by other known methods such as degradation of starch or soluble starch with an acid. As an acid degradation method to degrade a starch or a soluble starch with an acid to obtain a saccharified starch, a preferable example is a treatment using oxalic acid. Further, as the saccharified starch, a commercially available saccharified starch may be used. Examples of commercially available saccharified starches include Fujisyrup C-75S, Fujisyrup C-75, HMTP-75 and A-75 (all of them are manufactured by Kato Kagaku). Since those commercially available saccharified starches have different saccharification degrees, a saccharified starch which is suitable for carrying out the present invention can be selected.

A culture medium for culturing a microorganism used in the present embodiment may include, as an auxiliary raw material for compensating the saccharified starch, a common carbon source of a culture medium, such as glucose, fructose, xylose, saccharose, maltose, molasses, glycerol, mannitol, citric acid, etc. In addition, as a nitrogen source of the culture medium, an organic nitrogen source such as soybean powder, soybean flake, defatted soybean powder, edible soybean protein, soybean peptide, soybean flour, peptone, yeast extract, malt extract, meat extract, casamino acid, corn steep liquor, urea, etc., or an inorganic nitrogen source such as ammonium nitrate, ammonium sulfate, etc. may be contained in the culture medium for culturing a microorganism used in the present embodiment. Among them, a preferable example of the medium nitrogen source includes heat denatured defatted soybean and, in particular, those which have been heat-denatured at about 70 to 90° C. and from which an ethanol-soluble component was removed, are more preferable. Further, a culture medium for culturing a microorganism used in the present embodiment may contain, as a micronutrient source, inorganic salts comprising phosphoric acid, potassium, sodium, magnesium and/or calcium, metal ions such as iron, copper, zinc, manganese, nickel, cobalt, etc. and vitamins. Interalia, it is preferable that one or more inorganic salt(s) selected from the group consisting of phosphoric acid, potassium, sodium, magnesium and calcium is/are contained.

In addition, in order to increase the yield of highly unsaturated fatty acids, a culture medium for culturing a microorganism used in the present embodiment may contain, as a precursor of the highly unsaturated fatty acids, for example, hydrocarbons such as hexadecane and octadecane; fatty acids such as oleic acid and linolenic acid or a salt thereof; triacyl glycerol and fatty acid esters such as fatty acid ethyl ester, glycerin fatty acid ester, sorbitan fatty acid ester, etc.; fats or oils such as olive oil, soybean oil, rapeseed oil, cotton seed oil and palm oil. One kind only of the aforementioned compounds may be contained alone, or a combination of two or more of them may be contained.

The aforementioned carbon source, nitrogen source and other medium component may be added to a culture medium before initiation of culturing and/or to a culture medium during culturing. These medium components may be added at once, or may be added sequentially or by dividing into plural times with the lapse of time. These medium components may be added alone or by mixing them in advance, after sterilization. A method of sterilization, and an order of addition are not particularly limited. Preferably, it is desirable that a carbon source and a nitrogen source are separately sterilized, and it is desirable that salts are added before completion of the logarithmic growth, more preferably before the intermediate stage of the logarithmic growth. Regarding other medium components which have no influence on the concentration of phosphoric acid ion, potassium ion, sodium ion, magnesium ion and calcium ion, the time of addition is not particularly limited as far as those components have such a concentration that growth of a *Mortierella* microorganism is not inhibited.

Practically, it is desirable that a total amount of a carbon source to be added is generally about 0.1 to 40% by weight, preferably about 1 to 25% by weight, and a total amount of a nitrogen source to be added is about 0.01 to 10% by weight, preferably about 0.1 to 10% by weight. More preferably, a carbon source and a nitrogen source may be added during culturing, with the amount of initially added carbon source being 1 to 12% by weight and the amount of initially added nitrogen source being about 0.1 to 8% by weight. In addition, the amount of the aforementioned precursor of highly unsaturated fatty acids to be added is about 0.001 to 10%, preferably about 0.5 to 10% relative to the culture medium.

Culturing conditions are not particularly limited, and may be according to the conventional method. For example, a culturing temperature is about 5 to 40° C., preferably about 20 to 30° C. Alternatively, after a *Mortierella* microorganism is proliferated at about 20 to 30° C., culturing may be continued at about 5 to 20° C. to produce a highly unsaturated fatty acid. The pH of the culture medium is about 4 to 10, preferably about 5 to 8. Examples of the culturing method include aerated culture underagitation, shakeculture, static culture, etc. Culturing is usually performed for about 2 to 20 days. By culturing as mentioned above, a highly unsaturated fatty acid-containing lipid is produced and accumulated in the *Mortierella* microorganism. In the present invention, aerated culture under agitation using a liquid medium is preferable.

Next, the highly unsaturated fatty acid-containing lipid is collected from the thus obtained culture. Examples of said "culture" include a culture solution during the production of a lipid by culturing and the sterilized product thereof, or a culturing solution after completion of culturing and the sterilized product thereof, or cultured cells collected from each of them and the dried products thereof. As a method of collecting a highly unsaturated fatty acid-containing lipid from the aforementioned culture, the known method may be used. For example, an objective lipid may be collected from cultured cells by the following method.

After completion of culturing, cultured cells are obtained from the culture solution by a conventional solid-liquid separation method such as centrifugation and/or filtration. The cultured cells are preferably washed with water, ground and dried. Drying may be performed by lyophilization, air drying, etc. The dried cells are preferably treated by extraction with an organic solvent under a nitrogen stream. Examples of the organic solvent used include ether, hexane, methanol, ethanol, chloroform, dichloromethane, petroleum ether, etc. Alternatively, better result can be also obtained by an alternate extraction with methanol and petroleum ether, or an extraction using a solvent of one layer system of chloroform-methanol-water. Inter alia, it is preferable to perform extraction using hexane. By distilling an organic solvent off from the extract under reduced pressure, a lipid containing a highly unsaturated fatty acid of high concentration can be obtained. Alternatively, extraction may be performed using wet cells, in place of the aforementioned method. In this case, a solvent which is compatible with water such as methanol, ethanol, etc., or a mixed solvent compatible with water which contains the aforementioned solvent and water and/or other solvent is used. Other procedures are the same as described above.

As a second embodiment of the present invention, a process for producing a highly unsaturated fatty acid-containing lipid, which comprises culturing the aforementioned *Mortierella* microorganism using a culture medium containing (a) a starch or a soluble starch and (b) a saccharifying enzyme, and collecting a highly unsaturated fatty acid-containing lipid from the culture will be described. In the present embodiment, a saccharified starch produced from a starch or a soluble starch contained in the culture medium with a saccharifying enzyme is used as a medium carbon source. That is, in the present embodiment, saccharification of starch and culturing of a *Mortierella* microorganism are performed at the same time. More specifically, the process is such that a saccharifying enzyme is added to a culture medium containing a starch or a soluble starch as a carbon source to convert the starch or the soluble starch into a saccharified starch which is easily degraded by α-glycosidase produced by a *Mortierella* microorganism, and glucose which is produced from the saccharified starch by the α-glycosidase is assimilated by the *Mortierella* microorganism to produce a highly unsaturated fatty acid-containing lipid.

A starch used in the present embodiment is not particularly limited, but specific examples include rice starch, cane starch, potato starch, tapioca starch, wheat starch and corn starch, and the processed starch and α-starch thereof. Among starches, those which are soluble in hot water are called soluble starch.

As a saccharifying enzyme used in the present embodiment, any saccharifying enzyme may be used as far as it is an enzyme used for saccharification. Specifically, a saccharifying enzyme prepared from a saccharifying enzyme-producing microorganism and a commercially available saccharifying enzyme can be used as mentioned in the first embodiment. Examples of the saccharifying enzyme used in the present embodiment include, as in the first embodiment, an endo-type amylase such as α-amylase having random degradation patterns, and a β-amylase which cleaves maltose units from an end of a starch molecule are preferable, and also an exo-type amylase such as glucoamylase which sequentially degrades starch from a non-reducing end to produce glucose may be used. This is because, since glucose produced by glucoamylase is immediately assimilated by a *Mortierella* microorganism, adverse influences due to an increase in osmotic pressure of a culture medium are not caused.

The present embodiment is entirely the same as the first embodiment except that (a) a starch or a soluble starch and (b) a saccharifying enzyme are used as a medium component for culturing microorganism in place of the saccharified starch. The medium component for culturing microorganism in the present embodiment may contain the aforementioned saccharified starch.

Next, as a third embodiment of the present invention, a process for producing a highly unsaturated fatty acid-containing lipid, which comprises mixed-culturing the aforementioned *Mortierella* microorganism and saccharifying enzyme-producing microorganism with the use of a culture medium containing a starch or a soluble starch, and collecting a highly unsaturated fatty acid-containing lipid from the culture will be described. In the present embodiment, a saccharified starch produced by a saccharifying enzyme produced by a saccharifying enzyme-producing microorganism from a starch or a soluble starch contained in a culture medium is used as a medium carbon source. That is, the present embodiment is a process in which a saccharified starch is produced by mixed-culturing a saccharifying enzyme-producing microorganism used in the saccharification together with a *Mortierella* microorganism in a culture medium containing a starch or a soluble starch as a medium carbon source, and the Mortierella microorganism produces a highly unsaturated fatty acid-containing lipid from the saccharified starch.

In the present embodiment, a *Mortierella* microorganism is cultured as a main microorganism, and a saccharifying enzyme-producing microorganism is cultured as an auxiliary microorganism. As the saccharifying enzyme-producing microorganism, any microorganisms can be used as far as they are a microorganism which secretes a saccharifying enzyme, and examples thereof include filamentous fungus belonging to the genus *Aspergillus, Rhizopus* and *Trichoderma*, and bacteria belonging to *Bacillus, Microbacterium* and *Klebsiella*. Among them, as the saccharifying enzyme-producing microorganism, a fungus belonging to the genus *Aspergillus* which produces α-amylase is preferable and, in particular, *Aspergillus oryzae* and *Aspergillus kawachii* are more preferable. Also, a microorganism secreting the glucoamylase can be preferably used as an auxiliary microorganism. Examples of the glucoamylase-secreting microorganism include *Aspergillus* microorganisms and *Rhizopus* microorganisms. In addition, by simple-culturing a mutant or a genetically recombinant strain of a *Mortierella* microorganism which is imparted with the saccharifying enzyme-producing ability, the same effect as that of mixed-culturing with a saccharifying enzyme-producing microorganism can be obtained.

The present embodiment is entirely the same as the first embodiment, expect that a starch or a soluble starch is used as a medium component for culturing microorganism in place of the saccharified starch, and a *Mortierella* microorganism and a saccharifying enzyme-producing microorganism are mixed and cultured in place of the simple-culturing of a *Mortierella* microorganism. In addition, the medium component for culturing microorganism in the present embodiment may contain the aforementioned saccharified starch. In this case, it is preferable that a saccharification degree of the saccharified starch, that is, a ratio of reducing sugar/total sugar is about 0 to 80%, preferably about 0 to 70%. When a *Mortierella* microorganism and a succharifying enzyme-producing microorganism are mixed-cultured, both microorganisms may be cultured at the same time, or after one of the microorganisms is cultured to some extent, the other microorganism may be added to perform mixed-culturing.

A highly unsaturated fatty acid-containing lipid obtained by the above method can be used in various applications such as animal feeds and foods. It is preferable that the lipid contains one or more highly unsaturated fatty acid (s) selected from the group consisting of γ-linolenic acid, dihomo-γ-linolenic acid, arachidonic acid, eicosapentaenoic acid, mead acid, 6,9-octadecadienoic acid and 8,11-eicosadienoic acid. Separation and purification of such highly unsaturated fatty acid can be performed by solvent extraction and, after desolvation, by deacidification, decolorization, deodorization, gum removal or cooling separation according to the conventional methods. Preferable examples include the method described in International Publication WO98/39468.

EXAMPLES

The invention will be described in detail below by way of Examples, but it goes without saying that the present invention is not limited to them. A component composition in a culture medium is shown by % by weight in all cases.

Example 1

As an arachidonic acid-producing microorganism, *Mortierella* SAM2197 (FERM BP-6261) was used.

Each 5 L of the culture medium 1-A, 1-B and 1-C shown in Table 1 was prepared in a culturing tank with 10 L capacity, and inoculated with the pre-cultured solution prepared in advance by flask culturing, followed by culturing. The amylase-treated starch for a culture medium 1-A used herein was the starch obtained by adding α-amylase (manufactured by Wako Pure Chemical Industries, Ltd., code No.011-16881) to a starch and incubating at 37° C. for 30 minutes. A reducing sugar was measured by a Somogyi-Nelson method, and a total sugar was measured by a Phenol-$H_2SO_4$ method. As a result of the measurement, the reducing sugar/total sugar ratio of the amylase-treated starch for the culture medium 1-A was 38%, and the reducing sugar/total sugar ratio of the soluble starch for the culture medium 1-B was 0%.

After aerated culture under agitation for 7 days, the amount of the produced arachidonic acid of 4.2 g/L was obtained in the culture medium 1-A, 1.2 g/L in the culture medium 1-B, and 4.3 g/L in the culture medium 1-C. An amount of produced arachidonic acid was calculated as follows. That is, a culturing solution was filtered through filter paper to recover a cell cake, and cells were dried at 105° C. and weighed. A value of the weight after drying was divided by value of the volume of the culturing solution which was subjected to filtration, to obtain a dried cell concentration. About 20 mg of the dried cell piece was precisely weighed into a screw-capped test tube, to this were added 2 mL of hydrochloric acid-methanol solution and 1 mL of dichloromethane, and reacted at 50° C. for 3 hours. After the reaction, hexane was added to extract fatty acid methyl ester, and the recovered hexane layer was concentrated under reduced pressure. The resulting fatty acid methyl ester was dissolved in a prescribed amount of acetonitrile, fractionated by gas chromatography, and each fatty acid methyl ester was quantitated from the peak area. The result of quantitation was divided by the precisely weighed value of cell piece to obtain each fatty acid content per dried cell. The resulting each fatty acid content was multiplied by the dried cell concentration to obtain the produced amount of each fatty acid.

TABLE 1

| | Culture medium No. | | |
|---|---|---|---|
| | 1-A | 1-B | 1-C |
| Amylase-treated starch | 12% | 0% | 0% |
| Soluble starch | 0% | 12% | 0% |
| Glucose | 0% | 0% | 12% |
| Soybean powder | 3% | 3% | 3% |
| Soybean oil | 0.2% | 0.2% | 0.2% |
| Anti-foaming agent | 0.1% | 0.1% | 0.1% |
| Produced amount of arachidonic acid | 4.2 g/L | 1.2 g/L | 4.3 g/L |

As apparent from the above table, an amount of produced arachidonic acid was small in a culture medium using a soluble starch, however, by using a saccharified starch obtained by treatment of starch with amylase, a high produced amount of arachidonic acid, which is equivalent to that of a medium using glucose, was obtained.

Example 2

As an arachidonic acid-producing microorganism, *Mortierella* SAM2197 (FERM BP-6261) was used. A culture medium (50 mL) containing 24% of soluble starch and 1.5% of yeast extract was prepared in a 500 mL flask. The culture medium (50 mL) was inoculated with 1×10⁵ spores of Mortierella SAM2197, inoculated with each of various amounts of a spore suspension of *Aspergillus oryzae*, and cultured for 7 days under the condition of 28° C. and at 160 rpm. As a control, a culture medium containing 12% of glucose and 1.5% of yeast extract was prepared as described above, and inoculated with *Mortireilla* SAM2197 (FERMBP-6261), followed by culturing. On the 5$^{th}$ day of culturing, 12% of glucose was added, followed by culturing for 7 days under the condition of 28° C. and 160 rpm. As a result of culturing, as shown in Table 2, the amount of produced arachidonic acid was 0.56 g/L at maximum when an inoculation amount of an *Aspergillus oryzae* spore suspension was 0.1 mL, which is nearly 2-fold that of the case where a soluble starch was used in single culturing of *Mortierella* (0.3 g/L), and is a production amount equivalent to the case where glucose was used as a carbon source by single culturing. When the amount of *Aspergillus* spore inoculation was 1 mL, the amount of produced arachidonic acid was reduced, which suggests that the growth of *Mortierella* may be suppressed in some cases due to the influence of growth of Aspergillus. Thus, it has been proved that, in the case of mixed-culturing of a *Mortierella* microorganism and a saccharifying enzyme-producing microorganism, it is preferable to culture with the former being a main microorganism.

TABLE 2

| Carbon source | Inoculation amount of *Aspergillus* spore suspension | Amount of produced arachidonic acid |
|---|---|---|
| Soluble starch | 0 mL | 0.30 g/L |
| Soluble starch | 0.01 mL | 0.50 g/L |
| Soluble starch | 0.1 mL | 0.56 g/L |
| Soluble starch | 1 mL | 0.16 g/L |
| Glucose | 0 mL | 0.58 g/L |

Example 3

As an arachidonic acid-producing microorganism, *Mortierella alpine* CBS754.68 was used. A culture medium (50 mL) containing each 4.5% of various sugars shown in Table 3, and 1% of yeast extract was prepared in a 500 mL flask, and inoculated with 1×10³ spores, followed by culturing. Culturing was performed for 5 days under the condition of 28° C. and 100 rpm. A method for saccharification of the starch (2), (7) and (8) was conducted in such a manner that an α-amylase and a pullulanase were added to a starch, and incubated at 37° C. for 30 minutes. As α-amylase, amylase AD "Amano"1 (manufactured by Amano Enzyme Inc.) was used and, as pullulanase, pullulanase "Amano"3 (manufactured by Amano Enzyme Inc.) was used.

As a result of culturing, amounts of produced arachidonic acid as shown in Table 3 were obtained, and it was shown that the preferable range of saccharification degree as described above exists.

TABLE 3

| Carbon source | Reducing sugar/ total sugar ratio | Produced amount of arachidonic acid |
|---|---|---|
| Glucose | 100% | 0.65 g/L |
| Soluble starch (1) | 0% | 0.11 g/L |
| Saccharified starch (2) | 18% | 0.43 g/L |
| Saccharified starch (3) | 27% | 0.58 g/L |
| Saccharified starch (4) | 33% | 0.61 g/L |
| Saccharified starch (5) | 50% | 0.61 g/L |
| Saccharified starch (6) | 55% | 0.69 g/L |
| Saccharified starch (7) | 80% | 0.69 g/L |
| Saccharified starch (8) | 92% | 0.65 g/L |

Details of carbon source
(1) Stabilose K, manufactured by Matsutani Chemical Industry Co., Ltd.
(2) Starch saccharified with α-amylase and pullulanase
(3) Fujisyrup C-75S, manufactured by Kato Kagaku
(4) Fujisyrup C-75, manufactured by Kato Kagaku
(5) HMTP-75 (M-70), manufactured by Kato Kagaku
(6) A-75, manufactured by Kato Kagaku
(7) Starch saccharified with α-amylase and pullulanase
(8) Starch saccharified with α-amylase and pullulanase Example 4

As an arachidonic acid-producing microorganism, *Mortierella alpina* CBS754.68 was used. Seed culturing was performed using a culture medium containing yeast extract and glucose as a nutrient source, and inoculated into a culture medium which was prepared in a 50 L culturing tank for fermentation. A medium composition of the regular culturing was any of three sugar compositions of 4-A, 4-B and 4-C shown in Table 4, and the common medium composition other than sugar was soybean powder 4%, soybean oil 0.1%, $KH_2PO_4$ 0.3%, $Na_2SO_4$ 0.1%, $CaCl_2.2H_2O$ 0.05% and $MgCl_2.6H_2O$ 0.05%. The reducing sugar/total sugar ratio of the saccharified starch used was 30%.

As a result of culturing for 10 days, the amounts of produced arachidonic acid in the culture mediums 4-A, 4-B and 4-C were 13.5 g/L, 7 g/L and 13.3 g/L, respectively. As elucidated by this result, by using a saccharified starch, not only avoidance of growth inhibition due to high concentration of glucose, but also and reduction in the cost for culturing due to fewer feedings can be achieved.

TABLE 4

|  | Culture medium No. | | |
| --- | --- | --- | --- |
|  | 4-A | 4-B | 4-C |
|  | | Carbon source | |
|  | Glucose | Glucose | Saccharified starch |
| Initial sugar concentration | 1.8% | 6% | 6% |
| Flowing sugar concentration | | | |
| 1 day flowing | 4.1% | 0% | 0% |
| 2 day flowing | 4.1% | 6% | 6% |
| 3 day flowing | 3.6% | 6% | 6% |
| 4 day flowing | 2.7% | 0% | 0% |
| 5 day flowing | 1.7% | 0% | 0% |
| Total carbon source | 18% | 18% | 18% |
| Amount of produced arachidonic acid | 13.5 g/L | 7.0 g/L | 13.3 g/L |

Example 5

As a mead acid-producing microorganism, *Mortierella alpine* SAM1861 (National Institute of Bioscience and Human-Technology, Conditional deposition No. 3590, FERM BP-3590) was used and, as dihomo-γ-linolenic acid-producing microorganism, *Mortierella alpine* SAM1860 (National Institute of Bioscience and Human-Technology, conditional deposition No. 3589, FERM BP-3589) was used. Each of three kinds of culture mediums (50 mL) shown in Table 5 was prepared in a 500 mL flask, and inoculated with $1 \times 10^3$ spores to initiate culturing. Culturing was performed for 7 days under the condition of 24° C. and 100 rpm.

TABLE 5

|  | Culture medium No. | | |
| --- | --- | --- | --- |
|  | 5-A | 5-B | 5-C |
| Saccharified starch (*) | 5% | 0% | 0% |
| Soluble starch | 0% | 5% | 0% |
| Glucose | 0% | 0% | 5% |
| Soybean powder | 1.5% | 1.5% | 1.5% |
| $KH_2PO_4$ | 0.2% | 0.2% | 0.2% |

TABLE 5-continued

|  | Culture medium No. | | |
| --- | --- | --- | --- |
|  | 5-A | 5-B | 5-C |
| Anti-foaming agent | 0.1% | 0.1% | 0.1% |
| Strain: SAM1861 Amount of produced mead acid | 0.44 g/L | 0.12 g/L | 0.45 g/L |
| Strain: SAM1860 Amount of produced dihomo-γ-linolenic acid | 0.55 g/L | 0.20 g/L | 0.60 g/L |

(*) Saccharified starch having the reducing sugar/total sugar ratio = 35% was used.

In the case where a soluble starch is used for culturing, both of the amounts of produced mead acid and produced dihomo-γ-linolenic acid were low, however, by using a saccharified starch, a large production amount equivalent to that of a glucose culture medium was obtained.

INDUSTRIAL APPLICABILITY

According to the present invention, a starch which is less expensive than glucose conventionally used as a medium carbon source is used for culturing a Mortierella microorganism, thus the cost for raw materials of a culture medium can be reduced and, consequently, the cost for producing a highly unsaturated fatty acid-containing lipid can be reduced. In addition, by using a saccharified starch as a medium carbon source, an increase of osmotic pressure in the culture medium can be suppressed, resulting in an increase in the yield of a highly unsaturated fatty acid-containing lipid per carbon source. Since an increase of osmotic pressure can be suppressed as mentioned above, in the present invention, unlike the case using glucose as a medium carbon source, feeding culture is not necessarily conducted. Therefore, facilities, the number of works and working time in the culturing step can be saved and, consequently, the cost for producing a highly unsaturated fatty acid-containing lipid can be reduced.

The invention claimed is:

1. A process for producing a highly unsaturated fatty acid-containing lipid, which comprises culturing a microorganism belonging to the genus *Mortierella* subgenus *Mortierella* with the use of a culture medium containing a saccharified starch, and collecting a highly unsaturated fatty acid-containing lipid from the culture, wherein said saccharified starch has a saccharification degree of 30% to 92% and has productivity of a highly unsaturated fatty-acid-containing lipid comparable to that of glucose as a medium carbon source.

2. The process according to claim 1, wherein the saccharified starch is obtained by treating a starch or a soluble starch with a saccharifying enzyme.

3. A process for producing a highly unsaturated fatty acid-containing lipid, which comprises culturing a microorganism belonging to the genus *Mortierella* subgenus *Mortierella* with the use of a culture medium containing (a) a starch or a soluble starch and (b) a saccharifying enzyme, and collecting a highly unsaturated fatty acid-containing lipid from the culture, wherein a saccharified starch is produced from said starch or soluble starch contained in the culture medium with said saccharifying enzyme, and said saccharified starch has a saccharification degree of 30% to 92%, and has productivity of a highly unsaturated fatty-acid containing lipid comparable to that of glucose as a medium carbon source and wherein said saccharified starch is used as a medium carbon source.

4. A process for producing a highly unsaturated fatty acid-containing lipid, which comprises mixed-culturing a *Mortierella* microorganism and a microorganism producing a saccharifying enzyme with the use of a culture medium containing a starch or a soluble starch, and collecting a highly unsaturated fatty acid-containing lipid from the culture;

wherein said *Mortierella* microorganism is of genus *Mortierella* subgenus *Mortierella*;

wherein said microorganism producing a saccharifying enzyme is *Aspergillus oryzae* or *Aspergillus kawachii*;

wherein said *Mortierella* microorganism is cultured as a main microorganism and said saccharifying enzyme-producing microorganism is cultured as an auxiliary microorganism, and wherein a saccharified starch is produced by said saccharifying enzyme from said starch or said soluble starch and said saccharified starch has a saccharification degree of 30% to 92% and is used as a medium carbon source and wherein said saccharified starch has productivity of a highly unsaturated fatty-acid containing lipid comparable to that of glucose as a medium carbon source.

5. The process according to claim 1, wherein the microorganism belonging to the subgenus *Mortierella* is *Mortierella alpina* or *Mortierella alliacea*.

6. The process according to claim 1, wherein the highly unsaturated fatty acid is one or more fatty acid(s) selected from the group consisting of γ-linolenic acid, dihomo-γ-linolenic acid, arachidonic acid, eicosapentaenoic acid, mead acid, 6,9-octadecadienoic acid and 8,11-eicosadienoic acid.

7. The process according to claim 1, wherein said saccharified starch has a saccharification degree of 33% to 92%.

8. A process for producing a highly unsaturated fatty acid-containing lipid, which comprises culturing a microorganism belonging to the genus *Mortierella* subgenus *Mortierella* with the use of a culture medium containing a saccharified starch, and collecting a highly unsaturated fatty acid-containing lipid from the culture, wherein said saccharified starch has a saccharification degree of 30 to 92% and has productivity of a highly unsaturated fatty-acid-containing lipid comparable to that of glucose as a medium carbon source, and wherein the highly unsaturated fatty acid is one or more fatty acid(s) selected from the group consisting of arachidonic acid, γ-linolenic acid, dihomo-γ-linolenic acid, eicosapentaenoic acid, mead acid, 6,9-octadecadienoic acid and 8,11-eicosadienoic acid.

* * * * *